(12) United States Patent
Mani et al.

(10) Patent No.: US 9,388,298 B2
(45) Date of Patent: Jul. 12, 2016

(54) CARBOXYLATE-ALUMOXANES NUCLEATING AGENTS AND A PROCESS FOR THE PREPARATION THEREOF

(71) Applicant: COUNCIL OF SCIENTIFIC & INDUSTRIAL RESEARCH, New Delhi (IN)

(72) Inventors: Mohan Raj Mani, Pune (IN); Ramesh Chellaswamy, Pune (IN); Vijayamohanan Kunjikrishnan Pillai, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/655,925

(22) PCT Filed: Dec. 27, 2013

(86) PCT No.: PCT/IN2013/000807
§ 371 (c)(1),
(2) Date: Jun. 26, 2015

(87) PCT Pub. No.: WO2014/102825
PCT Pub. Date: Jul. 3, 2014

(65) Prior Publication Data
US 2015/0344672 A1    Dec. 3, 2015

(30) Foreign Application Priority Data
Dec. 27, 2012 (IN) ............... 4019/DEL/2012

(51) Int. Cl.
*C08K 5/56* (2006.01)
*C07F 5/06* (2006.01)
*C08K 5/098* (2006.01)
*C08K 5/00* (2006.01)

(52) U.S. Cl.
CPC . *C08K 5/56* (2013.01); *C07F 5/069* (2013.01); *C08K 5/098* (2013.01); *C08K 5/0083* (2013.01)

(58) Field of Classification Search
CPC .......... C07F 5/069; C08K 5/56; C08K 5/098; C08K 5/0083
USPC ......................................... 556/182, 183, 184
See application file for complete search history.

(56) References Cited

U.S. PATENT DOCUMENTS 6,369,183 B1 * 4/2002 Cook ................... C08G 2/00
525/326.1

OTHER PUBLICATIONS

Derakhshan et al., Powder Technology, vol. 226, pp. 117-129 (2012).*
Derakhshan et al., Powder Technology, vol. 225, pp. 156-166 (2012).*

* cited by examiner

*Primary Examiner* — Porfirio Nazario Gonzalez
(74) *Attorney, Agent, or Firm* — Norton Rose Fulbright US LLP (57) ABSTRACT

The present invention disclose an improved carboxylate-alumoxanes nano sheets nucleating agent of formula (I), for advanced nucleation of thermoplastic semi-crystalline polymer, at low concentration; [Formula should be inserted here] where $2x+y+z=3$ wherein; G represents a Phenyl ring or Naphthyl ring or fused aromatic rings R is independently selected from the group consisting of H,($C_1$-$C_6$)alkyl, ($C_1$-$C_6$)alkoxy, aryloxy, hydroxy, halogen, aryl, arylalkyl and carbocyclic ring with adjacent carbon atoms of the parent phenyl ring; E is either oxygen or a bond; F is either $CH_2$ or a bond; n=2–50.

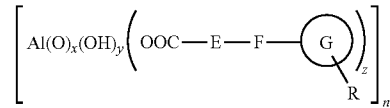

7 Claims, 10 Drawing Sheets

Fig. 1. DSC thermogram of iPP cooling curves

Ts- Self nucleated temperature
Tc- Crystallization temperature

Fig. 2. Plot of Ts vs. Tc

Fig. 3. Plot of Tc vs. Nucleation efficiency

CARBOXYLATE-ALUMOXANES NUCLEATING AGENTS AND A PROCESS FOR THE PREPARATION THEREOF

CROSS-REFERENCE TO RELATED APPLICATIONS

This application is a national phase application under 35 U.S.C. §371 of International Application No. PCT/IN2013/000807 filed 27 Dec. 2013, which claims priority to Indian Patent Application No. 4019/DEL/2012 filed 27 Dec. 2012. The entire contents of each of the above-referenced disclosures is specifically incorporated herein by reference without disclaimer.

FIELD OF THE INVENTION

The present invention relates to carboxylate-alumoxanes nano sheets nucleating agent of formula (I) for advanced nucleation of thermoplastic semi-crystalline polymer, at low concentration.

Further, the invention provides cost-effective, benign method for preparation of said nucleating agents that exhibit significant nucleation efficiency.

BACKGROUND OF THE INVENTION

Polyolefins are widely used in various industries such as food, pharmaceutical, agriculture, automobile which include preparation of moulding products such as kitchen ware, food containers, drink bottles, garden furniture, washing machine components, automotive parts, ropes, tapes, twines, fishing nets, flexible containers etc.

The use of polyolefins for the said applications requires improvement in impact strength, stiffness, heat resistance and fast injection moulding cycle times which are all achievable due to higher crystallization temperatures obtained when using high quality nucleating agents.

This improvement in the physical qualities of polyolefins can be achieved by using nucleating agents that give enhanced physical and clarifying properties to polymer.

Nucleating agents are generally inorganic materials with a small average particle size and a high melting point.

The use of nucleating agents is economically beneficial, as they increase the polymers' crystallization temperature, which leads to shorter processing cycles and associated energy savings. A sub-group of nucleating agents consists of 'clarifying' agents, i.e. additives that are used to improve the optical properties of a polymer.

Polypropylene is recognized as a relatively easy material to nucleate, where the rate of crystallization is low enough to allow the nucleating agent to have a direct impact on the nucleation density. Conversely, polyethylene has an extremely fast rate of crystallization, rendering most nucleating agents as ineffective. Further Isotactic polypropylene (iPP) is widely used polymer, due to its good mechanical properties and low price. However, iPP requires very high undercooling for crystallization to take place, due to its bulkier chains and more complex crystal unit cell arrangement compared to, polyethylene (PE). Thus, nucleating agents can offer a great advantage in industrial processing times, as well as significantly influence the solid-state structure of iPP.

Typical nucleating agents known in the art include minerals, such as chalk, clay, kaolin, talc, silicates, and the like. Organic nucleating agents, such as salts of aliphatic or aromatic carboxylic acids, aromatic salts, metallic salts of aromatic phosphorus compounds, quinaridones, aromatic amides, and polymers having melting points are more efficient.

A range of potential nucleating agents including organic acid derivatives, sorbitol derivatives, phosphorus-containing species, and inorganics are known in the art. Few representative examples of commercially available nucleating agents are described herein below.

Jansen et al, in Plastics Additives Handbook, by Gachter & Muller, pp. 862-875,1993, discloses nucleating agents and their effect on crystalline and semi-crystalline polymers.

U.S. Pat. No. 6,537,665 discloses certain alumina-coated silica nano-powders carrying a surface coating of an organic acid also function as polymer nucleating agents.

H. N. Beck in Journal of applied polymer science 11, pp. 673-685 (1967) discloses heterogeneous nucleating agents for polypropylene crystallization such as sodium benzoate and basic aluminum dibenzoate.

U.S. Pat. No. 6,913,829 describe nucleating agent, particularly alumina-coated silica particles bonded to benzoic acid, optionally in presence of surfactant.

Zhiping Lv et al. in Materials and Design 37 (2012) 73-78 reports design and properties of a titanium based nucleating agent for isotactic polypropylene (iPP) selected from group consisting of titanium ester, particularly TB, TD and TSD (titanate of benzoate or 4-tert-Butylbenzoate) and process for preparation thereof, wherein, silicon titanium esteri.e. (TSD) was found to be effective nucleating agent for crystallization of iPP.

U.S. Pat. No. 7,144,939 relates to the use of organic nucleating agents such as cyclic dicarboxylates, including metal salts of hexahydrophthalic acid (HHPA) to induce certain specific polymer crystalline orientations into the molded polypropylene articles and improved physical properties as well.

The effect of the calcium salts of suberic (Ca-Sub) and pimelic (Ca-Pim) acids additives on the crystallization, melting characteristics, and structure of isotactic polypropylene (iPP) was studied by József Vargaand reported in Journal of Applied Polymer Science 74. (10), pp 2357-2368, 1999.

Markus Blomenhofer et al. reported organic compounds, particularly substituted 1,3,5-benzenetrisamides, capable of selectively and extremely efficiently nucleating the growth of the common α-crystal modification of isotactic polypropylene (i-PP), in Macromolecules, 2005, 38 (9), pp 3688-3695

Further U.S. Pat. No. 4,536,531 describes use of carboxylic salts of alkali or alkali earth metals as nucleating agents for polyesters, wherein metal salts of aliphatic monocarboxylic acids such as acetic acid, propionic acid, caproic acid, palmitic acid, stearic acid, oleic acid, behenic acid, montanic acid etc. and suitable metals are sodium, potassium, lithium, magnesium, calcium, barium, and zinc.

JP 48074550 describes use of metal salts of aryl phosphonates such as calcium benzylphosphonate and aluminium phenyl phosphonate as nucleating agents for polyesters such as polybutylene terephthalate (PBT), wherein use of 0.5 wt % zinc phenylphosphonate in PBT improves the properties compared with PBT alone.

In view of above, many of the nucleants have shown effectiveness in increasing the nucleation density of thermoplastic polyesters such as PBT, PHA, whereas nucleation of semi-crystalline polymers requires aliphatic carboxylic acid, phosphoric acid etc.

Though the above nucleants or nucleating agents provide the sites or nuclei for initiating polymer crystallization, certain disadvantages are accompanied with it, such as agglomeration which can generate regions of stress concentration and in homogeneity in moulding, opaque products, environmentally undesirable and toxic; additionally some of the nucleating agents are commercially expensive and leads to poor crystallization. Thus, there is a need for benign and cost-effective class of nucleant which allow for the production of semi-crystalline thermoplastic polymer like polyolefins having high crystallinity, strength, dimensional stability.

U.S. Pat. No. 6,369,183 describes the preparation of polymer composite and hybrid polymers and resins in which at least one component is a chemically modified carboxylate-alumoxane. The carboxylate alumoxanes are chemically bonded into the polymer backbone through reaction of appropriate functional groups of the polymer precursor with carboxylate alumoxane at higher proportion (more than 5 wt %). Notably, it has not been used as nucleating agents. Where as in the present invention a tiny amount (3 ppm) of carboxylate-alumoxane is added to nucleate Polypropylene (PP) in order to speed up the crystallization of PP.

OBJECTIVES OF THE INVENTION

The main objective of the present invention is to provide carboxylate-alumoxanes nano sheets nucleating agent of formula (I) for advanced nucleation of thermoplastic semi-crystalline polymer at low concentration.

Another object of the present invention is to provide a carboxylate-alumoxanes nano sheets based nucleating agent for production of thermoplastic, semi-crystalline polymer at low concentration and a cost-effective, industrially viable process for preparation thereof.

Another object of the present invention is to provide a process for the preparation of carboxylate-alumoxanes nano sheets based nucleating agent of formula (I).

SUMMARY OF THE INVENTION

Accordingly, the present invention provides carboxylate-alumoxanes nano sheet nucleating agent of formula (I) for advanced nucleation of thermoplastic semi-crystalline polymer at low concentration Formula I Where $2x + y + z = 3$ wherein;
G represents a Phenyl ring or Naphthyl ring or fused aromatic rings
R is independently selected from the group consisting of H, $(C_1-C_6)$alkyl, $(C_1-C_6)$alkoxy, aryloxy, hydroxy, halogen, aryl, arylalkyl and carbocyclic ring with adjacent carbon atoms of the parent phenyl ring;
E is either oxygen or a bond;
F is either $CH_2$ or a bond
n=2-50

In one embodiment of the present invention carboxylate-alumoxanes nano sheet nucleating agent of formula (I) is represented by following compounds;
p-tert-Butybenzoate (PTBBA)-alumoxane;
Benzoate-alumoxane;
Phenoxyacetate-alumoxane;
2-Naphthoate-alumoxane;
4-methylbenzoate-alumoxane;
3-methylbenzoate alumoxane; and
2-methylbenzoate-alumoxane.

In another embodiment of the present invention the thermoplastic semi crystalline polymer is selected from the group consisting of polyethylene, polypropylene, polystyrene, copolymers of ethylene and propylene, copolymers of ethylene, polystyrene, polybutene-1 and polypentene selected from high density, low density, linear low density, isotactic, syndiotactic, heterotactic or atactic.

In still another embodiment of the present invention, the nucleating agent is used in an amount of at least about 0.0001 to 10 wt. % based on the weight of the polymer.

Another embodiment of the present invention provides a process for the preparation of carboxylate-alumoxanes nano sheet nucleating agent of formula (I), wherein said process comprises heating aqueous solution of aluminium nitrate at temperature ranging between 100° C. to 150° C. followed by adding freshly prepared ammonia drop wise to obtain peudo-boehmite/amorphous alumina gel then subsequently adding (un)substituted or substituted organic acid in the presence of a organic solvent into it and stirring this solution at temperature ranging between 100° C. to 150° C. for a period ranging between 1 hr to 3 hrs at 500 rpm to 1000 rpm to obtain carboxylate-alumoxanes.

Still in another embodiment of the present invention the molar ratio of aluminium nitrate to organic acid is varied between 5:1 to 1:10

Still in another embodiment of the present invention, the organic solvents used is selected from the group consisting of methanol, ethanol, ethylene glycol, 1- or 2-propanol, propylene glycol, glycerol, 2-methyl-2-propanol, 2-butanol, 1- or 2-pentanol, acetone, and tetrahydrofuran either alone or in combination with each other or with water.

Still in another embodiment of the present invention, the organic solvents used is selected from the group consisting of methanol, ethanol, 2-propanol or other higher alcohols, or mixtures of such alcohols with water to allow for easy removal of unreacted organic acid left in the product.

Still in another embodiment of the present invention, the organic acid is present in an amount ranging from 10 to 80% based on the weight of carboxylate-alumoxane.

Still in another embodiment of the present invention organic acid used is selected from the group consisting of p-tert-Butylbenzoic acid, benzoic acid, phenoxyacetic acid, 2-naphthoic acid, 4-methylbenzoic acid, 3-methylbenzoic acid and 2-methylbenzoic acid.

ABBREVIATIONS iPP: isotactic polypropylene
PBT: polybutylene terephthalate
NAs: nucleating agents

BRIEF DESCRIPTION OF THE DRAWINGS

FIG. 7 depicts FT-IR of Example 1 (PTBBA-Alumoxane) annealed at different temperature. The FT-IR spectra of PTBBA-alumoxanes (Example 1) show sharp peak in the range at 3697 $cm^{-1}$ and 988 $cm^{-1}$ is assigned to hydroxo bridged —OH stretching and bending vibrations respectively. The asymmetric ($v_{as}$) and symmetric ($v_s$) COO$^-$ stretching vibrations occurs at 1557 $cm^{-1}$ and 1439 $cm^{-1}$ respectively. The $\Delta(v_{as}\text{-}v_s)$ of 118 $cm^{-1}$ suggests that the carboxylate group is involved in bridged bidentate mode of coordination. The peak at 1693 $cm^{-1}$ corresponds to C=O stretching vibrations indicates the presence of mono coordinated —COO$^-$. However, this peak intensity is less which suggests that unidentate mode is in the minor proportion.

The sample annealed above 365° C. shows new peak at 833 $cm^{-1}$ and 691 $cm^{-1}$, which is absent in the unannealed sample. This indicates that annealing leads to a new structure/polymorph of PTBBA-alumoxane.

DETAILED DESCRIPTION OF INVENTION

The present invention provides a carboxylate-alumoxanes nano sheets based nucleating agent of formula (I);

Formula I

Where 2x + y + z = 3 wherein;
G represents a Phenyl ring or Naphthyl ring or fused aromatic rings
R is independently selected from the group consisting of H, $(C_1\text{-}C_6)$alkyl, $(C_1\text{-}C_6)$alkoxy, aryloxy, hydroxy, halogen, aryl, arylalkyl and carbocyclic ring with adjacent carbon atoms of the parent phenyl ring;
E is either oxygen or a bond;
F is either $CH_2$ or a bond
n=2-50

As disclosed hereinabove and below, the name carboxylate-alumoxane is based on the reference [A. R. Barron et al. Journal of Materials Chemistry (1995), 5(2), pp. 331-341] which describes the formation of carboxylate-alumoxane, [Al(O)x(OH)y(O2CR)z]n where 2x+y+z=3 and R=C1-C13, from the reaction of pseudo-boehmite, [Al(O)(OH)]n with carboxylic acid (RCO2H).

In the present invention, the organic acids are selected from aromatic acid either substituted or unsubstituted, wherein selection of organic acid is not limited to, benzoic acid or naphthoic acid.

The substituents are independently selected from the group consisting of (C1-C6)alkyl, (C1-C6)alkoxy, aryloxy, hydroxy, halogen, aryl, arylalkyl and carbocyclic ring with adjacent carbon atoms of the parent phenyl ring of the aromatic acid. Particularly the acids such as p-methyl benzoic acid, t-butyl benzoic acid, phenoxy acetic acid, 2-Naphthoxyacetic acid, 2-naphthoic acid or mixtures thereof are used that give excellent result.

The present invention relate to nucleating agents selected from the group consisting of:
1. p-tert-Butybenzoate (PTBBA)-alumoxane;
2. Benzoate-alumoxane;
3. Phenoxyacetate-alumoxane;
4. 2-Naphthoate-alumoxane;
5. Phenylacetate-alumoxane;
6. 4-methylbenzoate-alumoxane;
7. 3-methylbenzoate-alumoxane; and
8. 2-methylbenzoate-alumoxane
which are characterized by XRD, FT-IR given herein below.

In the invention, there is provided a method of preparing nucleant or nucleating agent for thermoplastic semi-crystalline polymers which comprises reaction of pseudoboehmite/amorphous alumina gel with organic acid in presence of suitable nucleating agent solvent.

In the instant process the solvent used for dissolving organic acids include but are not limited to $C_1$ to $C_6$ aliphatic mono, di- and tri-alcohols such as methanol, ethanol, ethylene glycol, 1- or 2-propanol, propylene glycol, glycerol, 2-methyl-2-propanol, 2-butanol, 1- or 2-pentanol; acetone, tetrahydrofuran and like thereof, further including mixtures of such solvents with each other or with water. Preferred nucleating agent solvents include methanol, ethanol, 2-propanol or other higher alcohols, or mixtures of such alcohols with water to allow for easy solvent removal.

The thermoplastic semi crystalline polymer used in the instant invention is particularly from the class of polyolefin, wherein the polymer is selected from the group consisting of polyethylene, polypropylene, polystyrene, copolymers of ethylene and propylene, copolymers of ethylene, polystyrene, polybutene-1, polypentene, which can be high density, low density, linear low density, isotactic, syndiotactic, heterotactic or atactic; preferably isotactic/syndiotactic, polypropylene and polystyrene.

The pseudoboehmite/amorphous alumina gel is reacted with organic acid compound, the relative amount of organic acid included in carboxylate-alumoxane can vary widely, and typically, the organic acid compound will be present in an amount of 10 to 80 wt. %, based on the weight of pseudoboehmite/amorphous alumina gel particles in the mixture.

In the instant case, no additional adjuncts or surfactant are added to the mixture to promote/intimate contact between the substrate particles and the organic acid compound.

The nano sheet inorganic-organic hybrid of alumoxane bonded with organic acid hereinafter referred as nucleant composition for use in advanced nucleation of semi-crystalline polymer.

The nucleant composition/hybrid of the invention preferably comprises pseudoboehmite/amorphous alumina gel and organic acid in molar ratios of about 5:1 to 1:20, when inorganic salt is used in a preferred nucleant composition, is in the range of 1:1 to 1:10, wherein such composition provides a suitable carboxylate-alumoxanes nano sheets to produce a polyolefin nucleant with desirable nucleation activity.

The nucleant composition of the invention, wherein the crude solid is separated and treated with suitable organic solvent, subsequently the solid product is powdered in any manner known to those skilled in the art and dried under vacuum.

The resulting powdered nano inorganic-organic hybrid nucleant is dispersed in to the desired thermoplastic semi crystalline polymer matrix.

The nucleant composition is in nano sheet structure, in which pseudoboehmite/amorphous alumina gel and bonded organic acid are arranged alternatively and the d-spacing between the adjacent alumoxane chains is present in the range of 9 Å to 25 Å

The invention further provides polyolefin and other thermoplastic polymer compositions containing the nucleants of the present invention as described in the above embodiments. The polymeric material is combined with the nucleants in any of a number of ways known to the skilled individual. Preferably, the polymer and nucleant are combined and melt extruded into strands which are crystallized and cut into pellets/powders. The pellets/powders so produced provide an advantageous form for use in processes where improved nucleation is desired.

The dispersion of instant nucleants in to the desired polymer matrix, preferably polyolefin accomplished by mixing the nucleating agent in powder form with the polymer immediately before it is molded, extruded or otherwise thermo-formed into a final product. The mixture of polymer and nucleants is further diluted with fresh polymer to get desired concentration range from 1 to 1000 ppm. The nucleation efficiency is measured by differential scanning calorimetry (DSC) and calculated from highest crystallization temperature (Tc) obtained for self-nucleated polymer.

In accordance with the present invention, the amount of inventive polymer nucleating agent of formula I that can be included in polymer compositions should be sufficient to produce a significant nucleating effect. In general the amount of nucleants used can be at least about 0.0001 to 10 wt. % based on the weight of the polymer. Particularly concentrations are in the range of about 0.001 to 0.5% based on the weight of the polymer.

The nucleant composition according to the invention may be useful for nucleation of polyolefin, other thermoplastic polymers etc. in an amount effective for increasing the crystallization rate of the polymer. Suitable levels of the nucleant composition to be added to the polyolefin or thermoplastic polymer range from about 0.01 to 10% based on the weight of the polymer.

DSC is an analytical technique which allows for precise determinations of enthalpy changes during an endothermic or exothermal event for studying the melting and crystallization characteristics of crystalline materials. If molten polymer is cooled at a constant rate, an exotherm may be produced as the polymer crystallizes. The temperature range over which the crystallization occurs, the area of the peak and the peak sharpness provide information about the crystallization behavior. The addition of a nucleating agent generally causes an increase in the crystallization peak temperature and the peak area.

Further the nucleating agents obtained from instant method are characterized by FTIR, XRD and TGA etc.

The nucleation study of instant carboxylate-alumoxanes nano sheets nucleant is demonstrated in table 1 wherein the preparation of specific nucleants is described in following examples.

EXAMPLES

Following are the examples given to further illustrate the invention and should not be construed to limit the scope of the present invention.

Nucleation Efficiency Study

The crystallization temperature of the bare PP and the crystallization temperature of the self-nucleated to the saturation limit provide the extreme situations needed to define an efficiency scale for any given polymer. The self-nucleation temperature (Ts) is fixed between peak temperature and just below the complete melting. The enthalpy of crystallization should be constant when the polymer is crystallized from various Ts. Producing very fine nuclei by partial melting of PP and allow the polymer to crystallize provide highest crystallization temperature (Tc max) experimentally possible. The blank PP crystallizes at lower temperature (Tcmin). So any nucleating agents crystallize PP at the temperature (TcNA) range between (Tcmax) and (Tcmin) if it has any efficiency at all. The epitaxial interaction of PP on polymer nucleating agent is always less favorable than crystallographic ones implicit in self-nucleated polymer even if the concentration is at saturation and dispersion is ideal. The nucleation efficiency as the following ratio:

$$NE = 100\frac{TcNA - Tcmin}{Tcmax - Tcmin}$$

TcNA-Crystallization Temperature Obtained from Nucleated Polymer

| S. No. | Nucleating agents | d-spacing of adjacent boehmite chains in the sheet | Crystallization temperature(Tc) (° C.) | Nucleation efficiency (%) |
|---|---|---|---|---|
| 1 | Pristine iPP | NA | 112.8 | 0 |
| 2. | Self-nucleated iPP sample | NA | 140.2 | 100 |

Example 1

Preparation of p-tert-Butybenzoate (PTBBA)-alumoxane 2.24 g (0.006 mol) of $Al(NO_3)_3 \cdot 9H_2O$ was taken in the 500 ml jacketed reactor equipped with overhead stirrer. 225 ml of deionized water was added and the solution was heated to 100° C. 6 ml of 5% of freshly prepared ammonia was added drop wise to produce pseudoboehmite/amorphous gel while it is stirred at 1000 rpm. After 10 mins 75 ml of isopropyl alcohol containing 2.12 g (0.012 mol) of p-tert-Butylbenzoic acid was added and the reaction mixture was stirred for 2 hrs at 100° C. at 1000 rpm. The white precipitate was separated by centrifugation and washed with 20 ml of methanol. This step repeated for five times. The product was powdered and dried under vacuum at 60° C. for about 12 hrs. Further, the white powder was kept in furnace at 300° C. for about 30 min.

FT-IR ($cm^{-1}$): 3696, 3423, 3069, 2963, 2905, 2870, 1932, 1804, 1693, 1604, 1556, 1517, 1436, 1363, 1316, 1269, 1196, 1160, 1108, 1018, 988, 791, 716, 607, 534 & 454.

WXRD 2θ peak positions: 6.6, 9.4, 13.4, 15.0, 17.2, 19.2, 21.3.

Example 2

Preparation of Benzoate-alumoxane 1.876 g (0.005 mol) of $Al(NO_3)_3 \cdot 9H_2O$ was taken in the 500 ml jacketed reactor equipped with overhead stirrer. 200 ml of deionized water was added and the solution was heated to 100° C. 5 ml of 5% of freshly prepared ammonia was added drop wise to produce pseudoboehmite/amorphous gel while it is stirred at 1000 rpm. After 10 mins 75 ml of isopropyl alcohol containing 6.12 g (0.05 mol) of benzoic acid was added and the reaction mixture was stirred for 2 hrs at 100° C. at 1000 rpm. The white precipitate was separated by centrifugation and washed with 20 ml of methanol. This step repeated for five times. The product was powdered and dried under vacuum at 70° C. for about 24 hrs.

FT-IR ($cm^{-1}$): 3675, 3425, 3066, 3030, 1694, 1604, 1559, 1496, 1436, 1315, 1281, 1179, 1158, 1069, 1027, 1002, 851, 825, 721, 686, 623, 548 & 433.

WXRD 2θ peak positions: 8.3, 14.0, 16.7, 18.3, 19.2, 22.5, 25.1, 27.3.

Example 3

Preparation of Phenoxyacetate-alumoxane 1.12 g (0.003 mol) of $Al(NO_3)_3 \cdot 9H_2O$ was taken in the 500 ml jacketed reactor equipped with overhead stirrer. 200 ml of deionized water was added and the solution was heated to 100° C. 3 ml of 5% of freshly prepared ammonia was added drop wise to produce pseudoboehmite/amorphous gel while it is stirred at 1000 rpm. After 10 mins 75 ml of isopropyl alcohol containing 4.56 g (0.03 mol) of phenoxyacetic acid was added and the reaction mixture was stirred for 2 hrs at 100° C. at 1000 rpm. The white precipitate was separated by centrifugation and washed with 20 ml of methanol. This step repeated for five times. The product was powdered and dried under vacuum at 70° C. for about 24 hrs.

FT-IR ($cm^{-1}$): 3607, 3523, 3062, 3042, 2945, 2912, 1617, 1495, 1472, 1432, 1343, 1303, 1265, 1220, 1175, 1154, 1086, 1071, 1020, 947, 884, 842, 790, 753, 729, 691, 631 & 509.

WXRD 2θ peak positions: 5.2, 12.8, 18.8, 23.6, 28.2.

Example 4

Preparation of 2-Naphthoate-alumoxane 0.25 gg (0.0006 mol) of $Al(NO_3)_3 \cdot 9H_2O$ was taken in the 500 ml jacketed reactor equipped with overhead stirrer. 200 ml of deionized water was added and the solution was heated to 100° C. 0.6 ml of 5% of freshly prepared ammonia was added drop wise to produce pseudoboehmite/amorphous gel while it is stirred at 1000 rpm After 10 mins 75 ml of isopropyl alcohol containing 1.03 g (0.006 mol) of 2-naphthoic acid was added and the reaction mixture was stirred for 2 hrs at 100° C. at 1000 rpm. The white precipitate was separated by centrifugation and washed with 20 ml of methanol. This step repeated for five times. The product was powdered and dried under vacuum at 70° C. for about 24 hrs.

FT-IR (cm$^{-1}$): 3674, 3424, 3060, 2958, 1692, 1631, 1603, 1591, 1566, 1559, 1507, 1479, 1429, 1366, 1269, 1242, 1208, 1152, 1139, 1112, 995, 981, 957, 916, 867, 830, 793, 764, 737, 645, 608, 526, 514 & 473.

WXRD 2θ peak positions: 7.0, 7.3, 14.0, 15.7, 18.7, 22.9.

Example 5

Preparation of Phenylacetate-alumoxane 0.94 gg (0.0025 mol) of Al(NO$_3$)$_3$.9H$_2$O was taken in the 500 ml jacketed reactor equipped with overhead stirrer. 100 ml of deionized water was added and the solution was heated to 100° C. 3 ml of 5% of freshly prepared ammonia was added drop wise to produce pseudoboehmite/amorphous gel while it is stirred at 1000 rpm. After 10 mins 75 ml of isopropyl alcohol containing 3.40 g (0.025 mol) of phenylacetic acid was added and the reaction mixture was stirred for 2 hrs at 100° C. at 1000 rpm. The white precipitate was separated by centrifugation and washed with 20 ml of methanol. This step repeated for five times. The product was powdered and dried under vacuum at 70° C. for about 24 hrs.

FT-IR (cm$^{-1}$): 3678, 3453, 3061, 3028, 2899, 2836, 1595, 1582, 1497, 1459, 1446, 1405, 1335, 1299, 1195, 1153, 1075, 1002, 846, 760, 730, 716, 696, 673, 621 & 594.

WXRD 2θ peak positions: 6.9, 7.6, 8.7, 9.6, 10.0, 10.7, 12.9, 13.8, 15.4, 17.2, 18.4, 19.3, 20.4, 21.4, 22.7, 24.4, 25.8, 27.2, 31.5, 34.8, 36.8.

Example 6

Preparation of 4-methylbenzoate-alumoxane 1.876 g (0.005 mol) of Al(NO$_3$)$_3$.9H$_2$O was taken in the 500 ml jacketed reactor equipped with overhead stirrer. 200 ml of deionized water was added and the solution was heated to 100° C. 5 ml of 5% of freshly prepared ammonia was added drop wise to produce pseudoboehmite/amorphous gel while it is stirred at 1000 rpm. After 10 mins 75 ml of isopropyl alcohol containing 6.80 g (0.05 mol) of 4-methylbenzoic acid was added and the reaction mixture was stirred for 2 hrs at 100° C. at 1000 rpm. The white precipitate was separated by centrifugation and washed with 20 ml of methanol. This step repeated for five times. The product was powdered and dried under vacuum at 70° C. for about 24 hrs.

FT-IR (cm$^{-1}$): 3697, 3430, 3063, 3037, 2921, 1929, 1807, 1694, 1602, 1558, 1515, 1436, 1293, 1248, 1210, 1183, 1113, 1099, 1021, 983, 850, 771, 695, 638, 530, 475 & 413.

WXRD 2θ peak positions: 7.3, 10.3, 14.7, 16.4, 20.5, 23.4, 30.6.

Example 7

Preparation of 3-methylbenzoate-alumoxane 1.876 g (0.005 mol) of Al(NO$_3$)$_3$.9H$_2$O was taken in the 500 ml jacketed reactor equipped with overhead stirrer. 200 ml of deionized water was added and the solution was heated to 100° C. 5 ml of 5% of freshly prepared ammonia was added drop wise to produce pseudoboehmite/amorphous gel while it is stirred at 1000 rpm. After 10 mins 75 ml of isopropyl alcohol containing 6.80 g (0.05 mol) of 3-methylbenzoic acid was added and the reaction mixture was stirred for 2 hrs at 100° C. at 1000 rpm. The white precipitate was separated by centrifugation and washed with 20 ml of methanol. This step repeated for five times. The product was powdered and dried under vacuum at 70° C. for about 24 hrs.

FT-IR (cm$^{-1}$): 3681, 3436, 3065, 3024, 2954, 2921, 1694, 1599, 1569, 1490, 1456, 1414, 1302, 1287, 1259, 1230, 1201, 1164, 1087, 988, 931, 898, 826, 802, 793, 760, 723, 677, 623, 549, 432.

WXRD 2θ peak positions: 7.5, 8.6, 10.8, 16.0, 18.4.

Example 8

Preparation of 2-methylbenzoate-alumoxane 1.876 g (0.005 mol) of Al(NO$_3$)$_3$.9H$_2$O was taken in the 500 ml jacketed reactor equipped with overhead stirrer. 200 ml of deionized water was added and the solution was heated to 100° C. 5 ml of 5% of freshly prepared ammonia was added drop wise to produce pseudoboehmite/amorphous gel while it is stirred at 1000 rpm. After 10 mins 75 ml of isopropyl alcohol containing 6.80 g (0.05 mol) of 2-methylbenzoic acid was added and the reaction mixture was stirred for 2 hrs at 100° C. at 1000 rpm. The white precipitate was separated by centrifugation and washed with 20 ml of methanol. This step repeated for five times. The product was powdered and dried under vacuum at 70° C. for about 24 hrs.

FT-IR (cm$^1$): 3674, 3437, 3060, 3022, 2967, 2931, 1608, 1587, 1559, 1490, 1447, 1419, 1382, 1290, 1198, 1163, 1107, 1052, 987, 862, 847, 822, 789, 742, 670, 700, 670, 617, 577, 529, 430.

WXRD 2θ peak positions: 7.3, 9.1, 16.4, 18.5, 23.0, 25.5.

Example 9

Dispersion of NAs Produced in Above Examples in to the Isotactic Polypropylene (iPP) Matrix The prepared polymer nucleating agents (NAs) Example 1 was compounded in to isotactic polypropylene (iPP) matrix using DSM twin-screw micro-extruder. The barrel temperature was maintained at 200° C. and the mixing time 3 min was followed for all extrusions. 5 g of powdered iPP was extruded with 0.2% (10 mg) of as produced nucleating agents (Example 1). Similarly iPP with 0.1% to 5% of nucleating agents was obtained. The PP with 0.2% NA was taken as a master batch and powdered by Retsch-cryo-mill. This was diluted with fresh iPP so as to produce PP extrudate with NA concentration range from 3 ppm to 1000 ppm. The nucleation efficiency was tested by differential scanning calorimetry. 4-6 mg of nucleated iPP was heated to 200° C. with ramp rate of 50° C./min and held for 2 min for complete melting followed by cooling to 30° C. with cooling rate of 10° C./min. The exothermic peak corresponds to crystallization was noted and compared with bare iPP. The nucleation efficiency was calculated from highest Tc obtained for self-nucleated iPP.

Example 10

Dispersion of NAs Produced from Example 1 in to the Syndiotacticpolypropylene (sPP) Matrix The prepared polymer nucleating agents (NAs) Example 1 was compounded in to sPP matrix using DSM twin-screw micro-extruder. The barrel temperature was maintained at 200° C. and the mixing time 3 min was followed for all extrusions. 5 g of powdered sPP was extruded with 0.2% (10 mg) of as produced nucleating agents (Example 1). The nucleation efficiency was tested by differential scanning calorimetry. 4-6 mg of nucleated sPP was heated to 200° C. with ramp rate of 50° C./min and held for 2 min for complete melting followed by cooling to 70° C. with cooling rate of 10° C./min. The exothermic peak corresponds to crystallization was noted and compared with bare sPP.

Example 11

Dispersion of NAs Produced from Example 1 in to the Syndiotactic Polystyrene (sPS) Matrix The prepared polymer nucleating agents (NAs) Example 1 was compounded in to sPS matrix using DSM twin-screw micro-extruder. The barrel temperature was maintained at 300° C. and the mixing time 3 min was followed for all extrusions. 5 g of powdered sPS was extruded with 1% (50 mg) of as produced nucleating agents (Example 1). Similarly, 0.2% to 5% composite was made. The nucleation efficiency was tested by differential scanning calorimetry. 4-6 mg of nucleated sPS was heated to 300° C. with ramp rate of 50° C./min and held for 2 min for complete melting followed by cooling to 30° C. with cooling rate of 10° C./min. The exothermic peak corresponds to crystallization was noted and compared with bare sPS.

Example 12

Dispersion of NAs Produced from Example 1 in to the Polyethylene Terephthalate (Pet) Matrix The prepared polymer nucleating agents (NAs) Example 1 was compounded in to PET matrix using DSM twin-screw micro-extruder. The barrel temperature was maintained at 290° C. and the mixing time 3 min was followed for all extrusions. 5 g of powdered PET was extruded with 2% (50 mg) of as produced nucleating agents (Example 1). Similarly 1% composite was made. The nucleation efficiency was tested by differential scanning calorimetry. 4-6 mg of nucleated PET was heated to 290° C. with ramp rate of 50° C./min and held for 2 min for complete melting followed by cooling to 30° C. with cooling rate of 10° C./min. The exothermic peak corresponds to crystallization was noted and compared with bare PET.

TABLE 1

| S. No. | Nucleating agent | Tc of syndiotactic polypropylene (sPP) (° C.) | Tc of syndiotactic polystyrene (sPS) (° C.) | Tc of polyethylene terephthalate (PET) (° C.) |
|---|---|---|---|---|
| 1 | Pristine polymer | 73.6 | 229.3 | 164.0 |
| 2. | Example 1 (p-tert-Butybenzoic acid-alumoxane layered hybrid) | 82.4 | 249.2 | 217.0 |

TABLE 2

Nucleation studies of unannealed and annealed PTBBA-alumoxane (Example 1) on isotactic polypropylene (iPP)

| PTBBA-alumoxane (NA) Annealing Temperature (° C.) | Isotactic polypropylene + 0.2 wt % NA Tc (° C.) | Nucleation efficiency (%) |
|---|---|---|
| Bare iPP | 113.0 | 0 |
| Self nucleatediPP | 140.2 | 100 |
| Unannealed | 128.6 | 56 |
| 260 | 130.5 | 63 |
| 300 | 132.3 | 70 |
| 350 | 131.5 | 67 |
| 365 | 130.8 | 64 |
| 380 | 130.5 | 63 |
| 430 | 128 | 54 |
| 1,3:2,4-bis(3,4-dimethylbenzylidene) sorbital (DMDBS) | 130.5 | 63 |

Figure 6:
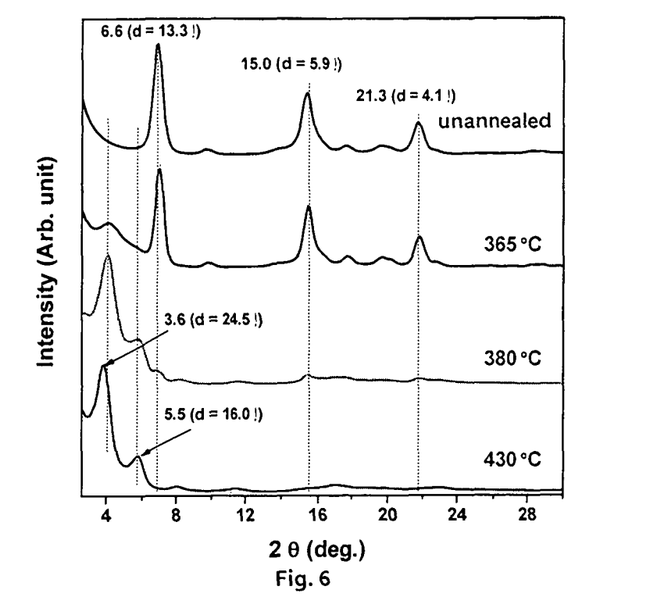
FIG. 6 depicts Powder X-ray diffraction pattern of Example 1 (PTBBA-Alumoxane) annealed at different temperature indicated on the graph. PTBBA-alumoxane, product of example 1, upon annealing transforms to a new polymorphic form. The sample annealed at 380° C. shows entirely different powder X-ray pattern as compared to unannealed sample indicating that annealing yields new polymorph of PTBBA-alumoxane.
Figure 7:
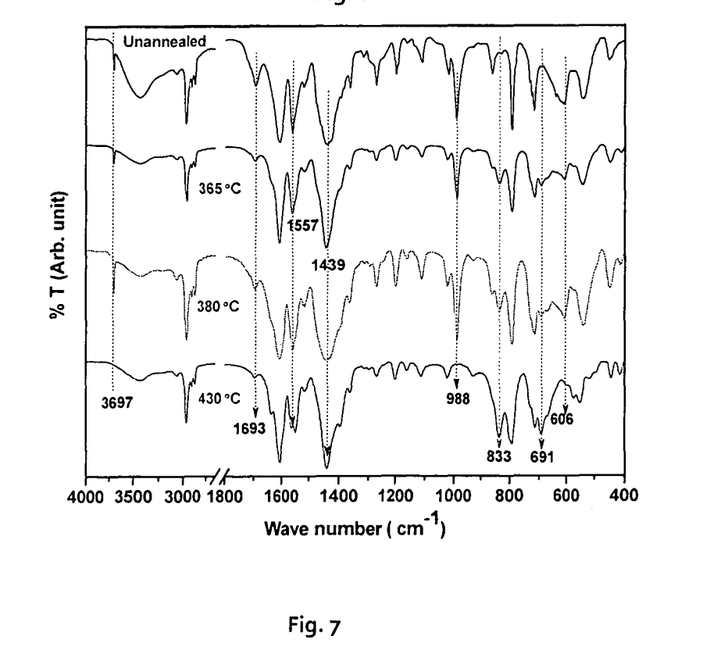
Figure 8:
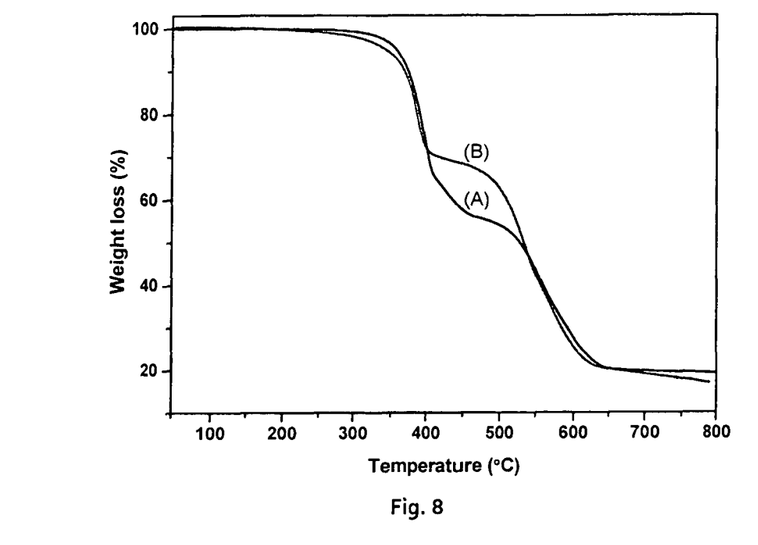
FIG. 8 depicts TGA of Example 1 (PTBBA-Alumoxane) annealed at (A) 300° C. and (B) 380° C.
Figure 9:
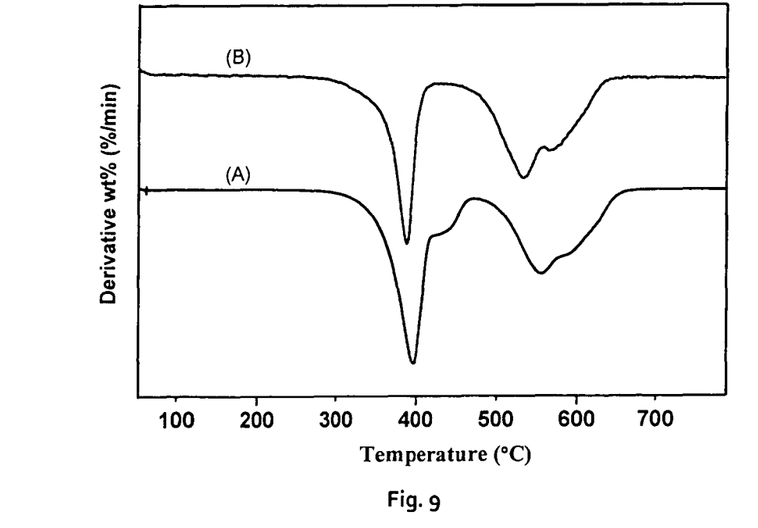
FIG. 9 depicts DTA of Example 1 (PTBBA-Alumoxane) annealed at (A) 300° C. and (B) 380° C.
Figure 10:
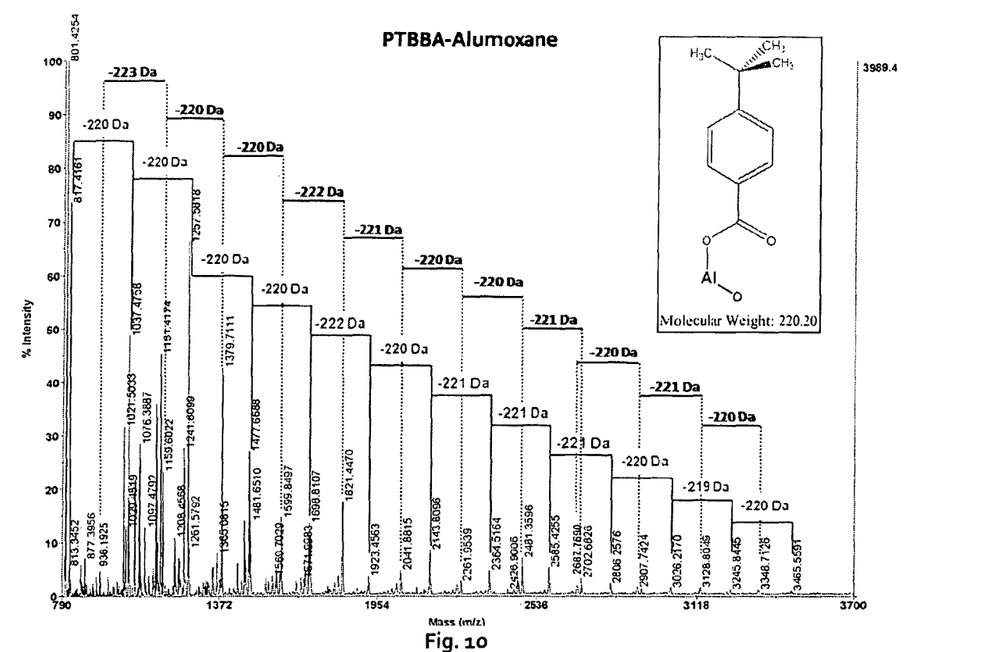
FIG. 10 depicts MALDI-TOF-MS of Example 1 (PTBBA-Alumoxane). The MALDI-TOF-MS of PTBBA-alumoxane shows that it is a high molecular weight multinuclear aluminium-PTBBA complex with repeating unit of [O—Al-PTBBA]. The appearance of multiple peak suggests that the product having different molecular weight species.
Figure 11:
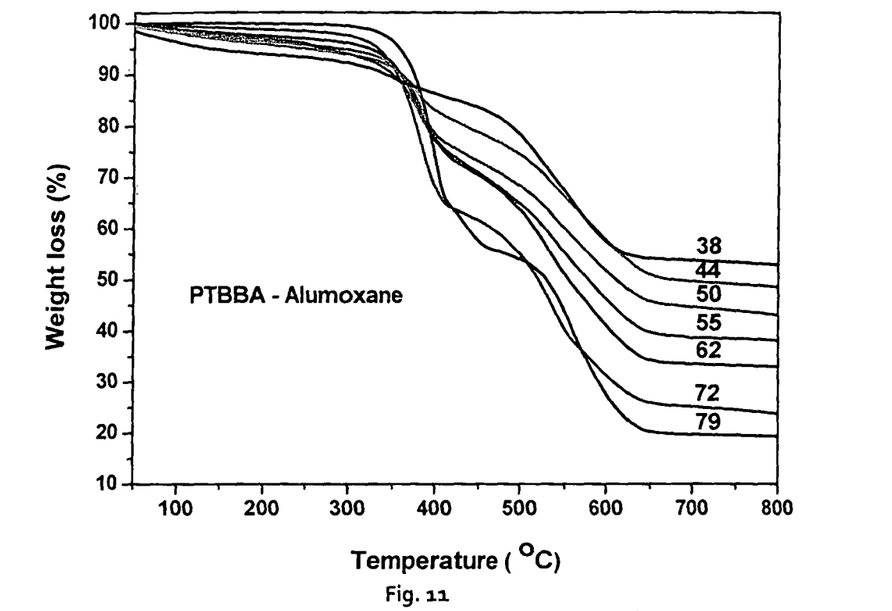
FIG. 11. TGA of Example 1 (Alumoxane with various % of PTBBA)
Figure 12:
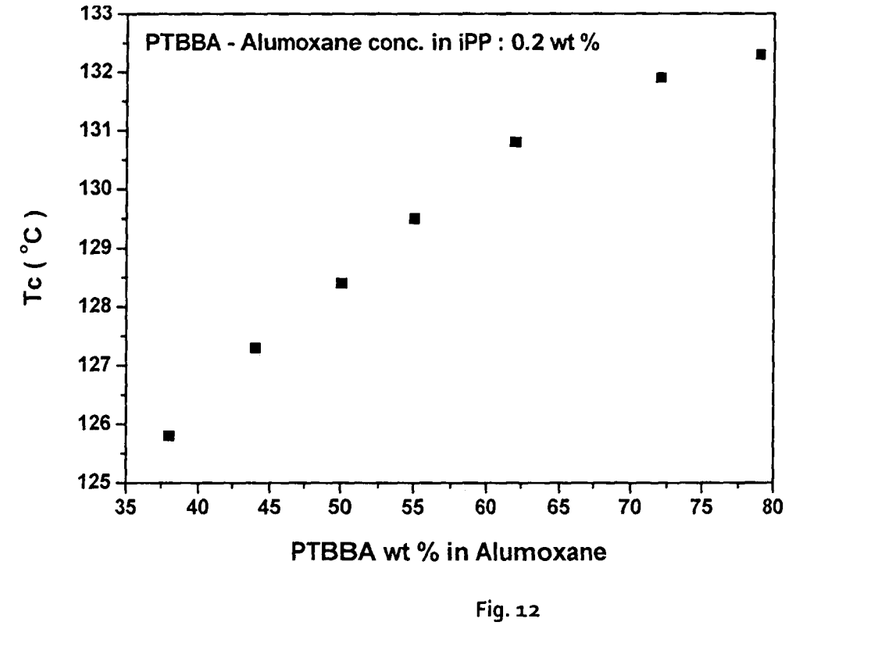
FIG. 12. depicts graph of PTBBA wt % in alumoxane Vs. Tc. 0.2 wt % Alumoxane with various % of PTBBA was dispersed into iPP matrix and the graph shows that the crystallization temperature of iPP increases as the PTBBA wt % in Alumoxane increases.
Figure 13:
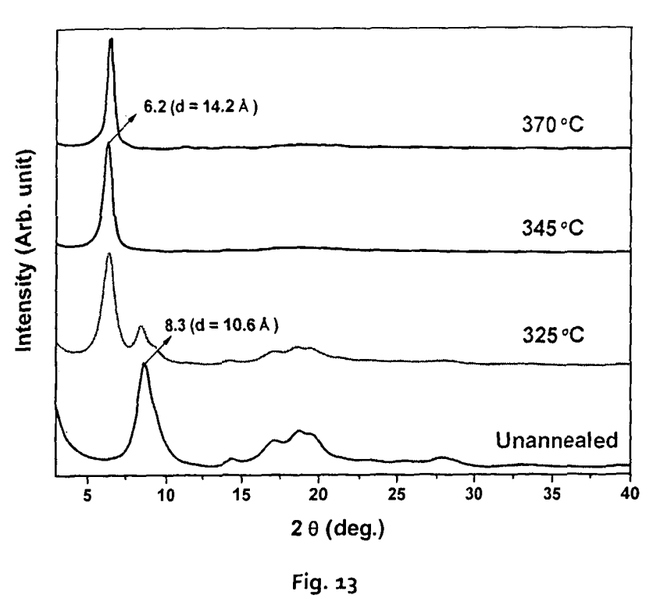
FIG. 13 depicts Powder X-ray diffraction pattern of Example 2 (Benzoate-Alumoxane) annealed at different temperature.
Figure 14:
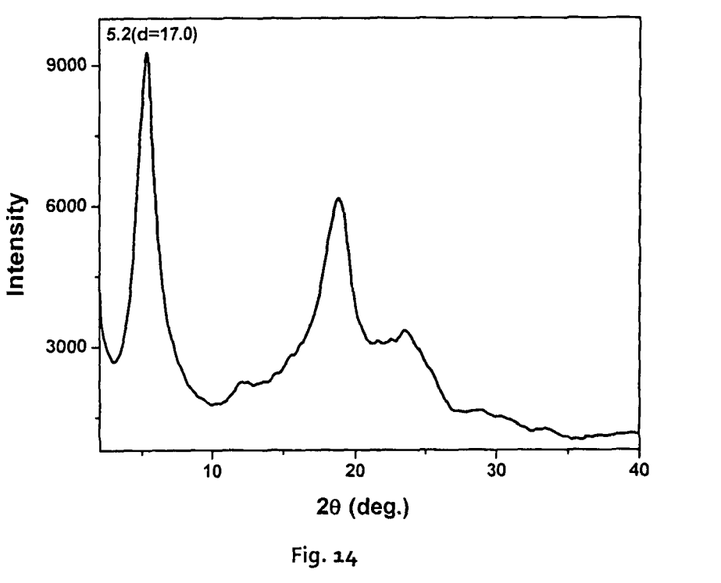
FIG. 14. Powder X-ray diffraction pattern of Example 3 (Phenoxyacetate-alumoxane)
Figure 15:
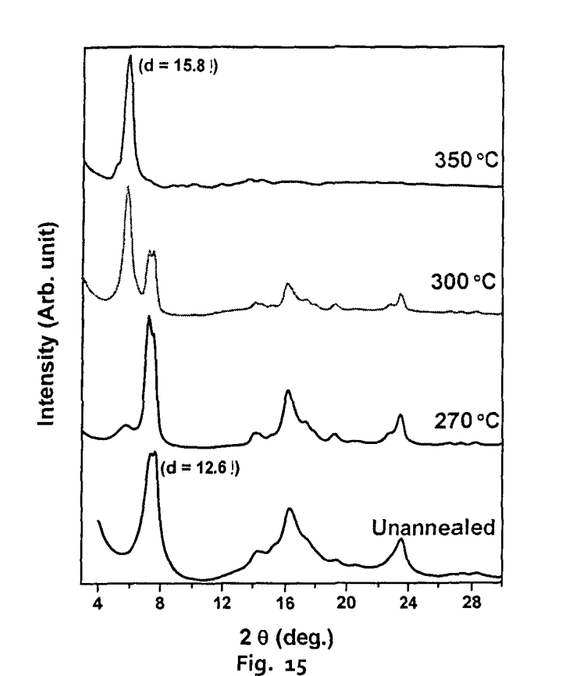
FIG. 15 depicts Powder X-ray diffraction pattern of Example 4 (2-Naphthoate Alumoxane) annealed at different temperature.
Figure 16:
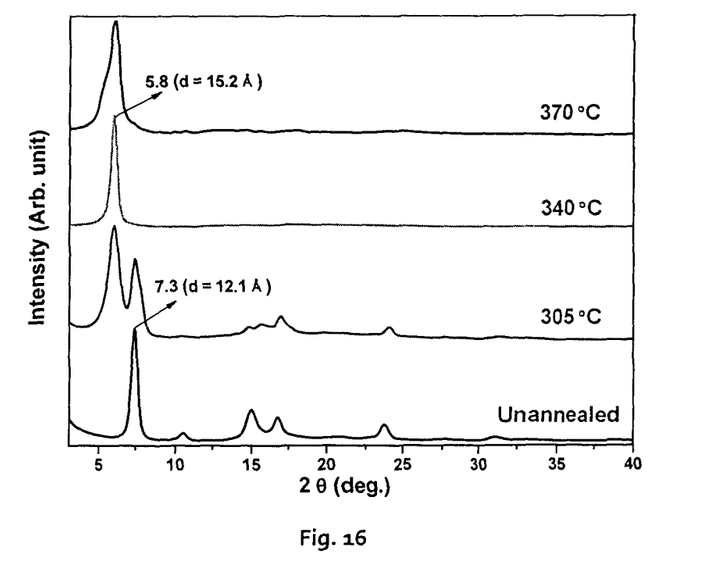
FIG. 16 depicts Powder X-ray diffraction pattern of Example 6 (4-methylbenzoate-Alumoxane) annealed at different temperature.
Figure 17:
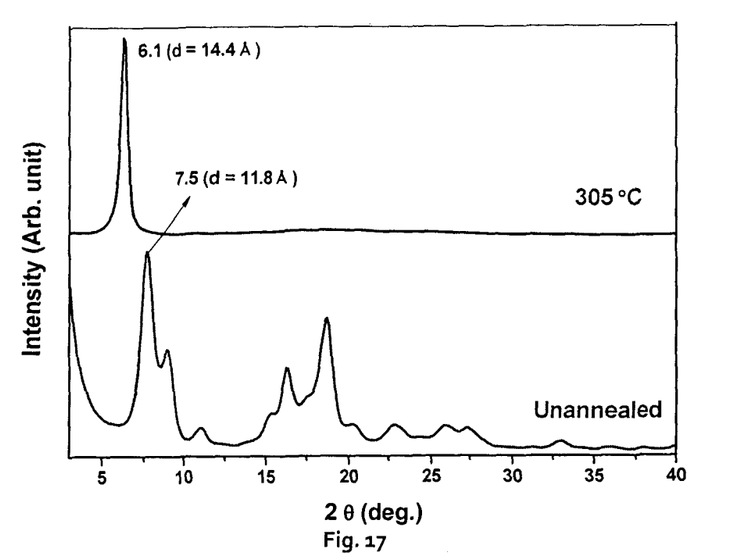
FIG. 17 depicts Powder X-ray diffraction pattern of Example 7 (3-methylbenzoate-Alumoxane) annealed at different temperature.
Figure 18:
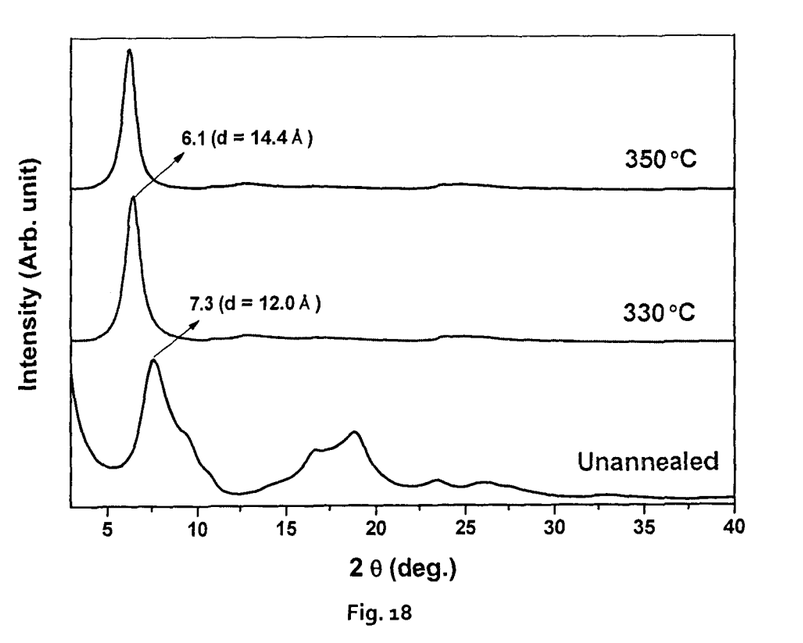
FIG. 18 depicts Powder X-ray diffraction pattern of Example 8 (2-methylbenzoate-Alumoxane)
Figure 19:
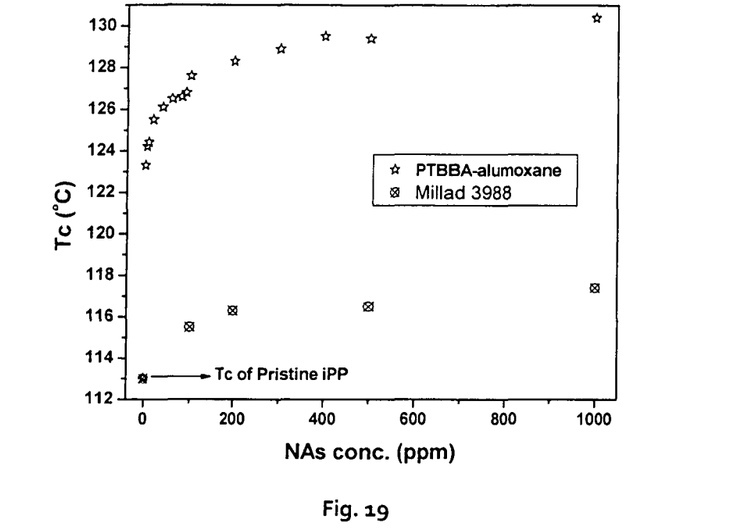
FIG. 19 The Graph shows crystallization temperature (Tc) of iPP nucleated by PTBBA-alumoxane with different concentration (in ppm) in comparison with pristine iPP and DMDBS. It is to be noted that the crystallization temperature of iPP is increased by 10° C. already at 3 ppm while DMDBS shows no major nucleation effect even at 1000 ppm. 400 ppm of PTBBA-alumoxane increases Tc by 17° C. which is equivalent to DMDBS at 2000 ppm.
Figure 20:
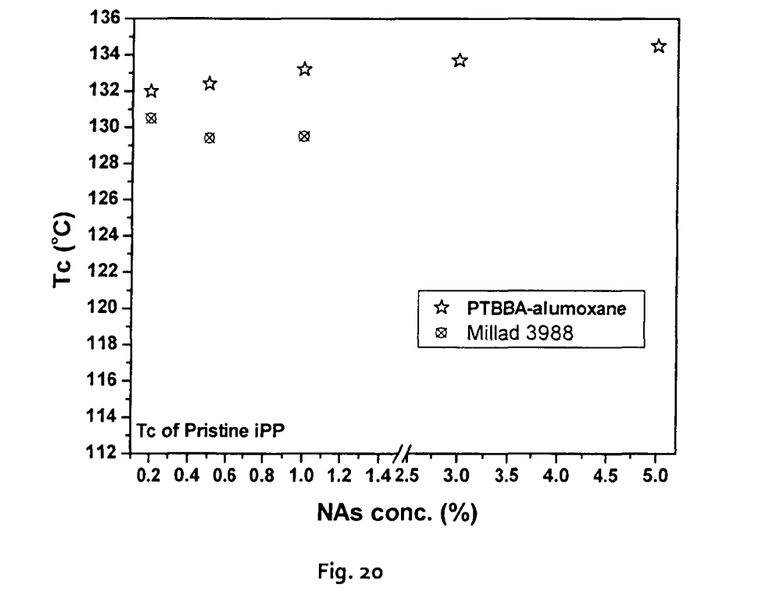
FIG. 20 The Graph shows crystallization temperature (Tc) of iPP nucleated by PTBBA-alumoxane with higher concentration (in %) in comparison with pristine iPP and DMDBS. The Tc of pristine iPP is 113° C.

Dispersion of 0.2 wt % of the PTBBA-alumoxane annealed at 300° C. shows 70% nucleation efficiency, which is higher as compared to DMDBS (DMDBS is most commonly used by many PP manufacturers to nucleate PP) at 0.2 wt %. PTBBA-alumoxane annealed at 380° C. shows that there is not much difference in nucleation efficiency although the crystalline structure is changed after annealing at 380° C. as shown in FIG. 6.)

The nucleation activity or efficiency study of iPP comprise following steps.

1. Bare iPP polymer was melted well above the melting temperature to erase the thermal history and obtain the Tc of unnucleated polymer by the cooling rate of 10° C./min, the Tc of 112.6° C. was registered and taken as Tc min (minimum crystallization temperature).

2. In the next cycle the polymer melted at 169.5° C. at this temperature partial melting occurs and considered as self-nucleated temperature (Ts). Held for 2 mins then cold the polymer with rate of 10° C./min to obtain the Tc 3. These two steps were repeated by changing the Ts to 169, 168, 167, 166° C.

4. The Tc of 140.2° C. was obtained when the polymer cold from 166° C. and taken as Tc max (maximum crystallization temperature)

Figure 1:
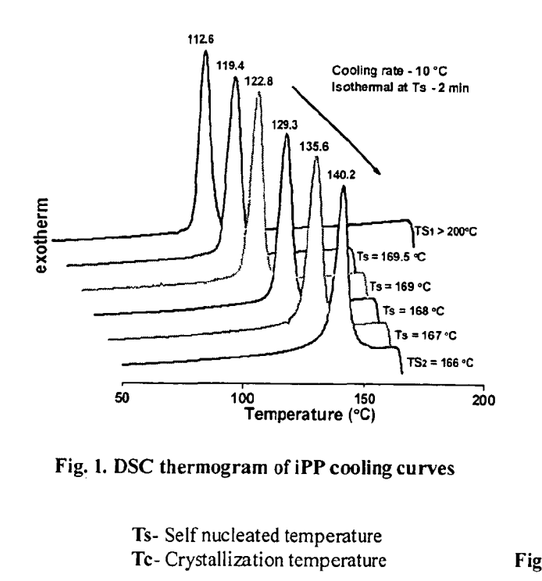
FIG. 1 depicts Nucleation Efficiency Study by Differential Scanning calorimetry of isotactic polypropylene
Figure 2:
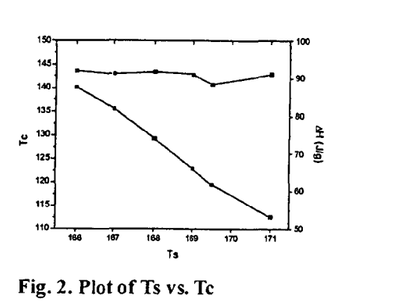
FIG. 2 depicts plot of self-nucleated temp (Ts) vs crystallization temp (Tc) of isotactic polypropylene
Figure 3:
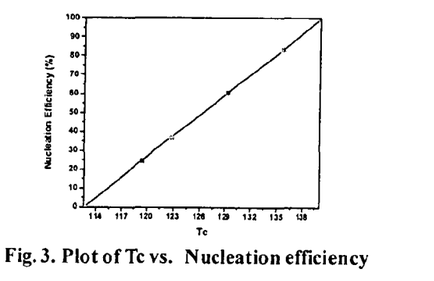
FIG. 3 depicts plot of crystallization temp (Tc) vs Nucleation efficiency of isotactic polypropylene
Figure 4:
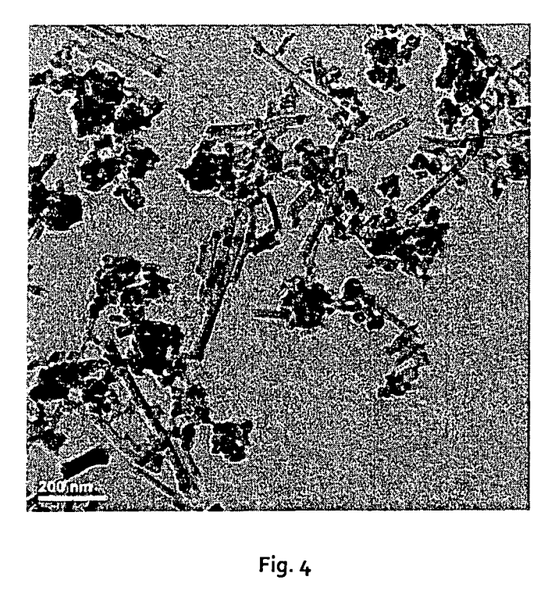
FIG. 4 depicts TEM image of Nucleant obtained from (p-tert-Butybenzoate-alumoxane Example 1.
Figure 5:
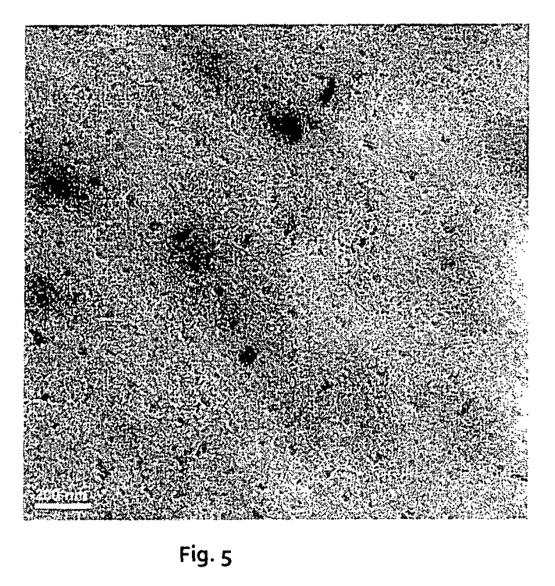
FIG. 5 depicts TEM image of iPP polymer with nucleant of Example 1.

5. The enthalpy of crystallization (ΔH) remains constant for the selected Ts. (FIG. 2)

6. The nucleation efficiency study of instant nucleants is characterized by means of differential scanning calorimetry (DSC).

Advantages of the Invention

1. Benign and cost-effective class of nucleant.
2. Allows for the production of semi-crystalline thermoplastic polymer like polyolefins having high crystallinity, strength, dimensional stability.

We claim:

1. Carboxylate-alumoxanes nano sheet nucleating agents for use in nucleation of thermoplastic semi-crystalline polymer at low concentration, said carboxylate-alumoxanes nano sheet nucleating agents represented by
  i) p-tert-Butybenzoate (PTBBA)-alumoxane;
  ii) Phenoxyacetate-alumoxane;
  iii) 2-Naphthoate-alumoxane;
  iv) 4-methylbenzoate-alumoxane;
  v) 3-methylbenzoate-alumoxane;
  vi) 2-methylbenzoate-alumoxane; and
  vii) phenylacetate-alumoxane.

2. The carboxylate-alumoxanes nano sheet nucleating agent according to claim 1, wherein the thermoplastic semi crystalline polymer is selected from the group consisting of polyethylene, polypropylene, polystyrene, copolymers of ethylene and propylene, copolymers of ethylene, polystyrene, polybutene-1, and polypentene selected from high density, low density, linear low density, isotactic, syndiotactic, heterotactic or atactic.

3. The carboxylate-alumoxanes nano sheet nucleating agent according to claim 1, wherein the nucleating agent is used in an amount of 0.0001 to 10 wt. % based on the weight of the polymer.

4. A process for the preparation of carboxylate-alumoxanes nano sheet nucleating agent as claimed in claim 1, wherein said process comprises heating aqueous solution of aluminium nitrate at a temperature ranging between 100° C. to 150° C. followed by adding freshly prepared ammonia drop wise to obtain peudoboehmite/amorphous alumina gel; adding an organic acid selected from the group consisting of p-tert-Butylbenzoic acid, phenoxyacetic acid, 2-naphthoic acid, 4-methylbenzoic acid, 3-methylbenzoic acid and 2-methylbenzoic acid in presence of an organic solvent to obtain a reaction mixture; and stirring the reaction mixture at a temperature ranging between 100° C. to 150° C. for a period ranging between 1 hr to 3 hrs at 500 rpm to 1000 rpm to obtain the carboxylate-alumoxanes nanosheet nucleating agent.

5. The process according to claim 4, wherein the molar ratio of aluminium nitrate to organic acid is in the range of 5:1 to 1:10.

6. The process according to claim 4, wherein the organic solvent is selected from the group consisting of methanol, ethanol and 2-propanol or a mixture thereof with water.

7. The process according to claim 4, wherein the organic acid is present in an amount ranging from 10 to 80% based on the weight of carboxylate-alumoxane.

* * * * *